United States Patent [19]

Saneyoshi et al.

[11] Patent Number: 4,916,121
[45] Date of Patent: Apr. 10, 1990

[54] ANTITUMOR COMPOSITION COMPRISING PYRIMIDINE TYPE NUCLEIC ACID DERIVATIVE AND 1-[(2-HYDROXYETHOXY)METHYL]URACIL DERIVATIVE

[75] Inventors: Mineo Saneyoshi, Sapporo; Takeo Kawaguchi, Tokyo; Masahiko Saito, Tokorozawa; Yoshiki Suzuki; Nobuaki Hanajima, both of Hino, all of Japan

[73] Assignee: Teijin Limited, Osaka, Japan

[21] Appl. No.: 860,390

[22] Filed: May 7, 1986

[30] Foreign Application Priority Data

May 7, 1985 [JP] Japan ................................ 60-95358
Aug. 8, 1985 [JP] Japan ............................... 60-173106

[51] Int. Cl.$^4$ .......................................... A61K 31/70
[52] U.S. Cl. ...................... 514/50; 514/49; 514/256
[58] Field of Search .............. 514/256, 43, 49, 46, 514/50, 45

[56] References Cited

PUBLICATIONS

Chadwick et al, *Cancer Research*, vol. 32, 1972, pp. 1045-1056.
*Cancer Research Supplement*, No. 3, pp. 1-125, 1955.
*Cancer Chemotherapy Reports*, vol. 1, pp. 1-109, 1959.
Sirotnak et al, *Cancer Research*, vol. 38, pp. 345-353, 1978.
Johnson et al, *Cancer Treatment Review*, vol. 2, pp. 1-31, 1975.

*Primary Examiner*—John W. Rollins
*Assistant Examiner*—Elli Peselev
*Attorney, Agent, or Firm*—Sughrue, Mion, Zinn, Macpeak & Seas

[57] ABSTRACT

An antitumor agent comprising (i) at least one pyrimidine type nucleic acid derivative having the general formula (I):

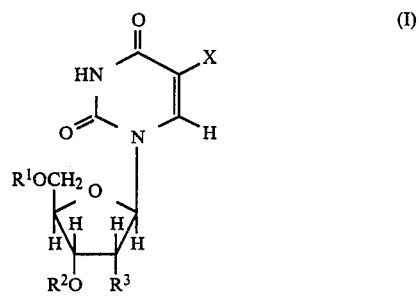

wherein X represents a fluorine atom or a trifluoromethyl group, $R^1$ and $R^2$ may be the same or different and represent a hydrogen atom or an acyl group, $R^3$ represents a hydrogen atom or a hydroxyl group, and (ii) at least one 1-[(2-hydroxyethoxy)methyl]uracil derivative having the general formula (II):

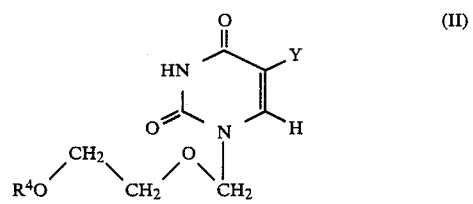

wherein Y represents a hydrogen atom, a halogen atom, a methyl group, a benzyl group, a benzyloxybenzyl group, a vinyl group, a nitro group, or an amino group and $R^4$ represents a hydrogen atom or an acyl group.

13 Claims, No Drawings

ANTITUMOR COMPOSITION COMPRISING PYRIMIDINE TYPE NUCLEIC ACID DERIVATIVE AND 1-[(2-HYDROXYETHOXY)METHYL]URACIL DERIVATIVE

BACKGROUND OF THE INVENTION

1. Field of the Invention

The present invention relates to an antitumor agent. More specifically, it relates to an antitumor agent containing, as effective ingredients, a pyrimidine type nucleic acid derivative and a 1-[(2-hydroxyethoxy)methyl]uracil derivative. In the antitumor agent of the present invention, the derivatives of 1-[(2-hydroxyethoxy)methyl]uracil are used in combination to inhibit decomposition of the pyrimidine type nucleic acid derivatives in living bodies when administered, whereby the utilization efficiency of 5-flouro-2'-de-oxyuridine in living bodies can be enhanced to exhibit an antitumor effect at a high level and a low dosage. The pyrimidine type nucleic acid derivative has an excellent antitumor activity in vitro, but a low effectiveness, for example, in oral administration.

2. Description of the Related Art

It has been reported that a pyrimidine type nucleic acid derivative including the acylated derivatives of 5-fluoro-2'-deoxyuridine has a higher by 10 to 100-fold antitumor activity in vitro as compared with a pyrimidine base derivative (see: Cancer Research, 35, 1121 (1975)).

Furthermore, it has been known in the art that 5-fluoro-2'-deoxyuridine is a compound having antitumor activity as one of the metabolites of 5-fluorouracil. Its antitumor activity has been reported to be 100-fold that of 5-fluoro-uracil at the same molar concentration, and 10 to 100-fold that of 5-fluorouridine, which is a metabolite of 5-fluorouracil, at the same concentration in inhibitory activity against the proliferation of an established cell line derived from a mouse in vitro (see: Cancer Res., 35, 1121 (1975); Cancer Res., 19, 494 (1959)).

However, in vivo tests using tumor-bearing animals, the effect of pyrimidine type nucleic acid derivatives is not sufficient, but contrary to the results in vitro, its antitumor effect has been reported to be inferior as compared with pyrimidine base derivatives such as 5-fluorouracil, and 5-fluorouridine (see: Cancer Res., 19, 494 (1959); Proc. Soc. Exp. Biol. Med., 97, 470 (1958); Proc. Soc. Exp. Biol. Mes., 104, 27 1960); Ann. N. Y. Acad. Sci., 76, 575 (1958).

Such results are considered to be attributable to the fact that pyrimidine type nucleic acid derivatives such as 5-fluoro-2'-deoxyuridine are rapidly decomposed by pyrimidine nucleoside phosphorylase such as uridine phosphorylase or thymidine phosphorylase in living bodies (see: Exp. Cell Res., Suppl. 9, 462 (1963); Biochem. Pharmac., 1, 328 (1959)), and further that 5-fluoro-2'-deoxyuridine has a shorter half-life in blood after administration in living bodies due to its physical and chemical properties to give an insufficient contact time with tumor cells (Cancer Res., 32, 1045 (1972); Clin. Pharmacol. Ther., 5, 581 (1964); Europ. J. Cancer, 16, 1087 (1980)).

For improving this drawback, studies have been heretofore made to chemically modify various pyrimidine type nucleic acids. For example, 3'-acyl-5-fluoro-2'-deoxyuridine (see: Japanese Unexamined Patent Publication (Kokai) No. 54-163586), 5-fluoro-2'-deoxyuridine acylated at the 3-position and at both the 3'- and 5'-positions (Japanese Unexamined Patent Publications (Kokai) Nos. 56-113795, 56-113796, 56-113797) are known. However, even in these derivatives, a satisfactory improvement is not obtained in potentiation of the antitumor effect.

Concerning 3',5'-diacyl-5-fluoro-2'-deoxyuridine, it is shown to have antitumor activity (Biochemical Pharmacology, 14, 1605 (1965)). Further, Japanese Unexamined Patent Publication (Kokai) No. 58-49315 discloses that said derivative has an antitumor activity at a lower dose as compared with 5-fluoro-2'-deoxyuridine.

However, since 3',5'-diacyl-5-fluoro-2'-deoxyuridine has a low water solubility, it can be applied for a preparation for injection of the prior art only with difficulty. On the other hand, when it is administered as an oral preparation, it has been reported to have a low antitumor effect, because it is mostly decomposed in the intestine in which esterase and uridine phosphorylase or thymidine phosphorylase activity is markedly greater as compared in other organs (Chem. Pharm. Bull., 33, 1652 (1985)).

On the other hand, 1-[(2-hydroxyethoxy) -methyl]uracils have been reported to become inhibitors against uridine phosphorylase in tumor cells and cytosol fractions of tumor cells and mouse liver (Biochem. Pharmac., 30, 2097 (1981); ibid, 31, 1857 (1982)). The effect of these compounds for pyrimidine nucleoside phosphorylase in normal digestive organs and the effect for pyrimidine nucleoside phosphorylase in normal liver homogenate have not been found at all. Further, there has been no reports of a simultaneous administration of a pyrimidine type nucleic acid derivative and a 1-[(2-hydroxyethoxy)methyl]uracil into the intestine by oral administration.

Accordingly, enhancement of the antitumor effect of 5-fluoro-2'-deoxyuridine by combined use of 1-[(2-hydroxyethoxy)methyl]uracils and 5-fluoro-2'-deoxyuridine may be considered. However, in this case, even when both may be administered at the same time, it is probable that the behavior of both in living bodies may differ, and therefore, it is not necessarily easy to obtain the effect of the combined use.

SUMMARY OF THE INVENTION

An object of the present invention is to eliminate the above-mentioned problems in the prior art and to provide an antitumor agent capable of improving the behavior of the pyrimidine type nucleic acid derivatives in living bodies and of administering it in the form which can prevent decomposition by uridine phosphorylase or thymidine phosphorylase in living bodies, and an excellent antitumor effect can be expected.

Other objects and advantages of the present invention will be apparent from the following description.

In accordance with the present invention, there is provided an antitumor agent containing, as effective ingredients, (i) at least one pyrimidine type nucleic acid derivative having the general formula (I) (i.e., component (i) or component (I)):

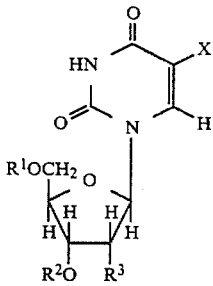

(I)

wherein X represents a fluorine atom or a trifluoromethyl group, $R^1$ and $R^2$ may be the same or different and represent a hydrogen atom or an acyl group, $R^3$ represents a hydrogen atom or a hydroxyl group, and (ii) at least one 1-[(2-hydroxyethoxy)methyl]uracil derivative having the general formula (II) (i.e., component (ii) or component (II):

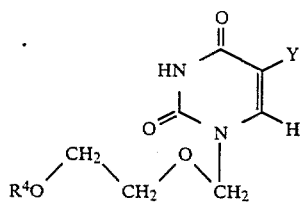

(II)

wherein Y represents a hydrogen atom, a halogen atom, a methyl group, a benzyl group, a benzyloxybenzyl group, a vinyl group, a nitro group, or an amino group and $R^4$ represents a hydrogen atom or an acyl group.

DESCRIPTION OF THE PREFERRED EMBODIMENTS

According to the present invention, the pyrimidine nucleic acid derivatives represented by the formula (I) and the 1-[(2-hydroxyethoxy)methyl]uracil derivatives represented by the formula (II) substantially coincide with each other in the behavior in living bodies when administered at the same time, and also are substantially the same in the rate of releasing 5-fluoro-2'-deoxyuridine and 1-[(2-hydroxyethoxy)methyl]uracil. Furthermore, an antitumor activity is not recognized in the 1-[(2-hydroxyethoxy)methyl]uracil derivatives represented by the formula (II) itself, but it can prevent decomposition of the pyrimidine type nucleic acid derivative represented by the formula (I) in the intestine by potently inhibiting the pyrimidine nucleoside phosphorylase activity existing in the intestine, thereby enabling oral administration.

When both the compound (I) and the compound (II) are administered at the same time, while no antitumor activity is recognized in the 1-[(2-hydroxyethoxy) methyl]uracil itself released, it can potently inhibit the uridine phosphorylase or thymidine phosphorylase activity existing in living bodies, thereby inhibiting decomposition of 5-flouro-2'-deoxyuridine released at the same time to enhance utilization efficiency and potentiate the antitumor activity.

In the pyrimidine type nucleic acid derivatives of the formula (I), $R^1$ and $R^2$ may be the same or different and represent hydrogen atom or acyl group. Examples of the acyl group include aliphatic acyl groups having 4 to 24 carbon atoms such as butyryl, hexanoyl, octanoyl, nonanoyl, decanoyl, dodecanoyl tetradecanoyl, hexadecanoyl, octadecanoyl, nonadecanoyl, eicosanoyl, docosanoyl, tetracosanoyl and the like, or aromatic acyl groups having 7 to 12 carbon atoms such as benzoyl, toluoyl and the like. The acyl group having 8 to 14 carbon atoms (e.g., octanoyl, decanoyl, dodecanoyl, tetradecanoyl) are more preferable. X in the formula (I) represents a fluorine atom or a trifluoromethyl group and $R^3$ represents a hydrogen atom or a hydroxyl group.

In the 1-[(2-hydroxyethoxy)methyl]uracils derivatives of the formula (II), Y represents a hydrogen atom, a halogen atom, a methyl group, a benzyl group, benzyloxybenzyl group, a vinyl group, a nitro group, or an amino group. Here, halogen atoms may preferably include a fluorine atom, iodine atom, chlorine atom, or bromine atom. $R^4$ represents a hydrogen atom or an acyl group and preferable examples of such an acyl group include aliphatic acyl groups having 2 to 24 carbon atoms such as acetyl, butyryl, hexanoyl, octanoyl, nonanoyl, decanoyl, octadecanoyl, hexadecanoyl, arachidonoyl, docosanoyl and the like, or aromatic acyl groups having 7 to 12 carbon atoms such as benzoyl, toluoyl and the like. As for the acyl group of $R^4$, the acyl group having 16 to 22 carbon atoms (e.g., hexadecanoyl, octadecanoyl, eicosanoyl, docosanoyl) are more preferable.

The pyridimine type nucleic acid derivatives represented by the formula (I) is a known compound, and these can be prepared in the same or similar manner as the known method (see: Biochemical Pharmacology, 14, 1605 (1965) and Proceeding Society Experimental Biology and Medicine (N. Y.), 97, 470 (1958). For example, they can be prepared by allowing 5-fluoro-2'-deoxyuridine and acid halide or acid anhydride or corresponding carboxylic acid to react with each other in the presence of a base such as trimethylamine, pyridine, etc.

The derivatives of 1-[(2-hydroxyethoxy)methyl]uracils represented by the formula (II) are a known or novel compound and these can be prepared in the same or similar manner as the known method [Journal of the Medicinal Chemistry 24, 753 (1981)]. More specifically, it can be produced according to the modification process of the so-called Hilbert-Johnson reaction in which, for example, a 5-substituted uracil represented by the following formula (II'):

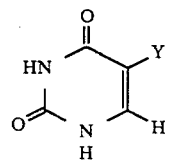

II' wherein Y is the same as defined above,
is allowed to react with 2-acyloxyethoxymethyl chloride in the presence of hexamthyldisilazane and trimethylsilyl chloride.

Typical examples of the pyrimidine type nucleic acid derivatives of the formula (I) to be used in the present invention include the following examples.

(1) 5-fluoro-2'-deoxyuridine,
(2) 5-trifluoro-2'-deoxyuridine,
(3) 5-fluorouridine.
(4) 3',5'-dibutyryl-5-fluoro-2'-deoxyuridine
(5) 3'-hexanoyl-5'-benzoyl-5-fluoro-2'-deoxyuridine (6) 3'5'-ditetradecanoyl-5-fluoro-2'-deoxyuridine
(7) 3'5'-dihexadecanoyl-5-fluoro-2'-deoxyuridine
(8) 3'-dodecanoyl-5'-toluoyl-5-fluoro-2'-deoxyuridine
(9) 3'5'-didodecanoyl-5-fluoro-2'-deoxyuridine
(10) 3'5'-dibenzoyl-5-fluoro-2'-deoxyuridine Typical examples of the derivatives of 1-[(2-hydroxyethoxy)methyl]uracil of the formula (II) to be used in the present invention include the following compounds.
(11) 1-[(2-hydroxyethoxy)methyl]-5-methyluracil,
(12) 1-[(2-hydroxyethoxy)methyl]-5-bromouracil,
(13) 1-[(2-hydroxyethoxy)methyl]-5-iodouracil,
(14) 1-[(2-hydroxyethoxy)methyl]-5-aminouracil,
(15) 1-[(2-hydroxyethoxy)methyl]-5-fluorouracil,
(16) 1-[(2-hydroxyethoxy)methyl]-5-nitrouracil,
(17) 1-[(2-hydroxyethoxy)methyl]uracil.
(18) 1-[[2-(octanoyloxy)ethoxy]methyl]-5-methyl-uracil
(19) 1-[[2-(octadecanoyloxy)ethoxy]methyl]-5-methyluracil
(20) 1-[[2-(hexadecanoyloxy)ethoxy]methyl]-5-iodouracil
(21) 1-[[2-(hexadecanoyloxy)ethoxy]methyl]-5-benzyluracil
(22) 1-[[2-(acetyloxy)ethoxy]methyl]-5-vinyluracil
(23) 1-[[2-(benzoyloxy)ethoxy]methyl]-5-methyluracil In the antitumor agent of the present invention, the combination of the component (i) in which $R^1$ and $R^2$ are acyl groups and $R^3$ is a hydrogen atom with the component (ii) in which $R^4$ is an acyl group, or the combination of the component (i) in which $R^1$, $R^2$, and $R^3$ are hydrogen atoms with the component (ii) in which $R^4$ is an hydrogen atom is preferable.

In the antitumor agent of the present invention, typical examples of preferable combinations of the component (i) and the component (ii) may include the following combinations.
(a) 3'5'-ditetradecanoyl-5-fluoro-2'-deoxyuridine and 1-[[2-(octadecanoyloxy)ethoxy]methyl]-5-methyluracil,
(b) 3',5'-didodecanoyl-5-fluoro-2'-deoxyuridine and 1-[[2-(hexadecanoyloxy)ethoxy]methyl]5-methyluracil,
(c) 3',5'-toluoyl-5-didecanoyl-2'-deoxyuridine and 1-[[2-(dodecanoyloxy)ethoxy]methyl]-5-bromouracil, and
(d) 5-fluoro-2'-deoxyuridine and 1-[(2-hydroxyethoxy)methyl]uracil.

In the antitumor agent of the present invention, the proportions of the pyrimidine type nucleic acid derivative represented by the formula (I), and the 1-[(2-hydroxyethoxymethyl]uracil derivative represented by the formula (II), may vary depending on the compounds selected, but it is generally recommendable to use 0.1 to 20 mols, preferably 0.5 to 5 mols, of the latter per 1 mol of the former.

In the present invention, it is preferable to formulate previously both the compound represented by the formula (I) and the compound represented by the formula (II) and incorporate the formulated composition in one preparation to be administered.

Also, in the present invention, it is preferable to formulate orally administrable preparations containing both the compounds represented by the formulae (I) and (II).

Further, in the present invention, the embodiment comprising a kit of preparations, containing the pyrimidine type nucleic acid derivatives and 1-[(2-hydroxyethoxy)methyl]uracil derivatives in separate preparations, respectively, is also included.

The antitumor agent of the present invention is preferably in the form of tablets, granules, grains, or capsules filled with granules or grains therein. These preparations can be prepared in a conventional manner by the use of excipients, binders, etc., conventionally used.

Examples of the preparation forms of the antitumor agent of the present invention to be administered include orally administratable preparations such as tablets, capsules, granules, pills, powders an liquids as well as parenterally administratable preparations such as aqueos injectable preparations, non-aqueous injectable preparations, suppositories, transdermal preparations.

Among these preparation forms, orally administrable preparations and suppositories are preferred. These preparations can be prepared according to conventional methods with the use of conventional carriers, excipients, auxiliary agents, binders, lubricants, and disintegrating agents, etc.

The antitumor agent of the present invention is particularly preferably in the form of tablets, granules, grains, etc., coated with an enteric soluble substance. Preferable examples of the enteric soluble substance include cellulose acetate phthalate, hydroxypropylmethyl cellulose phthalate, copolymers of methyl methacrylate and methacrylic acid, etc.

For coating an enteric soluble substance, an enteric soluble substance may be dissolved in an appropriate solvent, and the solution applied on tablets, granules, etc., according to the pan coating method, the fluidized layer coating method, etc.

The amount of pyrimidine type nucleic acid derivatives to be formulated in the preparation to be administered of the antitumor agent according to the present invention depends on the kind of derivative and cannot be particularly limited, but the dose for clinical use may be generally 0.5 to 50 mg/kg, more preferably 1.0 to 10 mg/kg, per day. The amount of the derivatives of 1-[(2-hydroxyethoxy)methyl]uracil can be determined from the formulation ratio as specified above.

The antitumor agent thus obtained comprising active ingredients of pyrimidine type nucleic acid derivatives and a 1-[(2-hydroxyethoxy)methyl]uracil derivatives, which is a phosphorylase inhibitor, exhibits high antitumor activities in oral administration and can be used as a pharmaceutical which can exhibit excellent pharmacological activities against liver cancer, gallbladder cancer, stomach cancer, lung cancer, esophagus cancer, colon cancer, kidney cancer, skin cancer, etc.

EXAMPLES

The present invention now will be further illustrated by, but is by no means limited to, the following Test Examples and Examples.

Test Example 1

Measurement of Lipid Solubilities of Acylated Derivative of 5-Flouro-2'-deoxyuridine and Acylated Derivative of 1-(2-Hydroxyethoxy)methyl uracil The retention time of the compounds of the present invention in reversed phase system high performance liquid chromatograph (Lichrosorb RP-18 column) was measured in two kinds of solvent systems. The compounds, solvent systems and the retention times of the compounds are shown in Table 1.

TABLE 1

Retention Time of Acylated Derivative of 5-Fluoro-
2'-deoxyuridine and Acylated Derivative of 1-[(2-
Hydroxyethoxy)methyl]uracil in Reversed Phase
System Liquid Chromatograph
[Column: Rechrosolve RP-18 4.0 × 130 mm, flow rate
1.2 ml/min.]

| | Retention time | |
|---|---|---|
| Compound | (a) Acetonitrile:water (19:1) | (b) Acetonitrile:acetic acid (999:1) |
| 1-[[2-(Hexadecanoyloxy)-ethoxy]-methyl]-5-methyluracil | 3.53 min. | 3.15 min. |
| 3',5'-Didodecanoyl-5-fluoro-2'-deoxyuridine | 3.96 min. | 3.00 min. |

As can be seen from Table 1, for example, 3'5'-didodecanoyl-5-fluorouridine (one of the compounds represented by the formula (I) has substantially the same retention time as 1-[[2-(hexadecanoyloxy)ethoxy]-methyl]-5-methyluracil (one of the compounds represented by the formula (II)), and therefore both compounds also have an equal lipid solubility and the behavior in living bodies based on lipid solubility of the compounds may be considered to be similar.

Test Example 2

Measurement of Hydrophilic Properties of Acylated Derivative of 5-Fluoro-2'-deoxyuridine and Acylated Derivative of 1-[(2-Hydroxyethoxy)methyl]uracil The retention times of the compounds of the present invention in normal phase system high performance liquid chromatograph (Nucleosil) 5 CN column were measured.

The compounds, solvent systems and the retention times of the compounds are shown in Table 2.

TABLE 2

Retention Time of Acylated Derivative of 5-Fluoro-
2'-deoxyuridine and Acylated Derivative of
1-[(2-Hydroxyethoxy)methyl]uracil in Normal Phase
System High Performance Liquid Chromatograph
[Column: Nucleosil 5CN, 5 μm, 4.6 id × 300 mm,
solvent system: n-hexane: ethanol = 88:12
1.2 ml/min.]

| Compound | Retention time |
|---|---|
| 1-[[2-(Eicosanoyloxy)ethoxy]methyl]-5-methyluracil | 5.48 min. |
| 3',5'-Ditetradecanoyl-5-fluoro-2'-deoxyuridine | 5.38 min. |

As can be seen from Table 2, for example, 3',5'-ditetradecanoyl-5-fluoro-2'-deoxyuridine (one of the compounds represented by the formula (I), has substantially the same retention time as 1-[[2-(eicosanoyloxy) ethoxy]methyl]-5-methyluracil (one of the compounds represented by the formula (II)), and therefore, the hydrophilic properties of the both compounds are equal and their behavior in living bodies based on the hydrophilic properties of the compounds may be considered to be the same.

Test Example 3

Measurement of Enzymatic Hydrolyzability of Acylated Derivative of 5-Flouro-2'-deoxyuridine and Acylated Derivative of 1-[(2-Hydroxyethoxy)methyl]uracil The hydrolysis rates of the compounds of the present invention were measured at 37° C. in rat duodenum epithelial homogenate (1%, w/v; pH 7.0). The compounds and the hydrolysis rate constants are shown in Table 3.

TABLE 3

Hydrolysis Rate of Acylated Derivative of 5-Fluoro-
2'-deoxyuridine and Acylated Derivative of 1-[(2-
Hydroxyethoxy)methyl]uracil in Rat Duodenum Homogenate

| Compound | Hydrolysis rate constant (min.$^{-1}$) |
|---|---|
| 1-[[2-(Eicosanoyloxy)ethoxy]methyl]-5-methyluracil | 0.052 |
| 3',5'-Ditetradecanoyl-5-fluoro-2'-deoxyuridine | 0.027 |

As can be seen from Table 3, for example, 3',5'-ditetradecanoyl-5-fluoro-2'-deoxyuridine (one of the compounds represented by the formula (I)) has an enzymatic hydrolyzability which is equal to that of 1-[[2-(eicosanoyloxy)ethoxy]methyl]-5-methyluracil (one of the compounds represented by the formula (II)), and therefore, when both compounds are administered to living bodies at the same time, the rates of release of 5-fluoro-2'-deoxyuridine and 1-[(2-hydroxyethoxy)methyl]-5-methyluracil respectively by the hydrolysis with enzyme systems in living bodies may be considered to be the same.

Test Example 4

Assay of Antitumor Activity by Simultaneous Administration of Acrylated Derivative of 5-Fluoro-2'-deoxyuridine and Acylated Derivative of 1-[(2-Hydroxyethoxy)methyl]uracil The antitumor effect for mouse leukemia L1210 by a simultaneous oral administration of the compounds of the present invention 3',5'-didodecanoyl-5-fluoro-2'-deoxyuridine and 1-[[2-(octadecanoyloxy)ethoxy]methyl]-5-methyluracil was compared with those of (a) 5-fluoro-2'-deoxyuridine alone, (b) 3',5'-didodecanoyl-5-fluoro-2'-deoxyuridine alone, and (c) a simultaneous oral administration of 3',5'-didodecanoyl-5-fluoro-2'-deoxyuridine and 1-[(2-hydroxyethoxy)methyl]-5-methyluracil.

$10^5$ ascite tumor cells of mouse leukemia L1210 7 days after transplantation were transplanted intraperioneally into mouse (♂ 8 weeks, Ca 25–26 g, 5 mice/group) and provided for experiments. 24 hours after transplantation of the tumor cells, the pharmaceuticals were administered orally three times on day 1, day 3 and day 5.

The antitumor effect of the pharmaceuticals were shown by the increase in life span (ILS) of the group administered with pharamaceuticals relative to the control group (with no pharmaceutical administered) (line extension %). The results are shown in Table 4.

TABLE 4

Antitumor Actities of the Pharmaceuticals of
the Invention and Control Pharmaceuticals

| | Dose of pharmaceutical administered mg/kg/one dose | | | | |
|---|---|---|---|---|---|
| | 5-Fluoro-2'-deoxy-uridine | 3',5'-Di-dodecanoyl-5-fluoro-2'-deoxy-uridine | 1-[[2-Octa-decanoyl-oxy)ethoxy methyl]-5-methyl-uracil | 1-[(2-Hydroxy ethoxy)-methyl]-5-methyl-uracil | ILS (%) |
| Control pharma-ceutical | 10 | — | — | — | 15 |
| | 30 | — | — | — | 10 |
| | 100 | — | — | — | 15 |

TABLE 4-continued

Antitumor Acitities of the Pharmaceuticals of the Invention and Control Pharmaceuticals

| | Dose of pharmaceutical administered mg/kg/one dose | | | | |
|---|---|---|---|---|---|
| | 5-Fluoro-2'-deoxy-uridine | 3',5'-Di-dodecanoyl-5-fluoro-2'-deoxy-uridine | 1-[[2-Octa-decanoyl-oxy)ethoxy methyl]-5-methyl-uracil | 1-[(2-Hydroxy ethoxy)-methyl]-5-methyl-uracil | ILS (%) |
| | 300 | — | — | — | 10 |
| Control pharma-ceutical | — | 10 | — | — | 0 |
| | — | 30 | — | — | 5 |
| | — | 100 | — | — | 15 |
| | — | 300 | — | — | 40 |
| Control pharma-ceutical | — | 30 | — | 20 | 32 |
| | — | 100 | — | 67 | 37 |
| | — | 300 | — | 200 | 46 |
| Pharma-ceutical of the invention | — | 10 | 15 | — | 34 |
| | — | 30 | 45 | — | 46 |
| | — | 100 | 150 | — | 46 |
| | — | 300 | 450 | — | 46 |
| | — | — | 450 | — | 12 |
| | — | — | — | 200 | 12 |

As can be seen from Table 4, simultaneous administration of 3',5'-didodecanoyl-5-fluoro-2'-deoxyuridine and 1-[[2-(octadecanoyloxy)ethoxy]methyl]-5-methyluracil, which is one combination of the compounds of the present invention exhibited a higher antitumor effect at a lower dose as compared with a single administration of 5-fluoro-2'-deoxyuridine or 3',5'-didodecanoyl-5-flouro-2'-deoxy uridine. Also, the effect was higher as compared with the case the phosphorylase inhibitor to be administered simultaneously with 3',5'-didodecanoyl-5-fluoro-2'-deoxyuridine is 1-[(2-hydroxyethoxy)methyl]-5-methyluracil, which was not converted into an acylated derivative.

Test Example 5

Pyrimidine Nucleoside Phosphorylase Activity in Various Organs of Rat

The pyrimidine nucleoside phosphorylase activities in homogenates of the small intestine, liver, kidney and plasma of SD-strain rats were assayed and compared in phosphate buffers of pH 7.0 containing respective enzyme systems at 37° C. with the decomposition rate of 5-fluoro-2'-deoxyuridine (one of the pyrimidine type nucleic acid derivative represented by the formula (I) as defined in the claim 1) as the index.

The concentrations of the homogenates and the plasma and the decomposition rate constants of 5-fluoro-2'-deoxyuridine (10 μg/ml) are shown in Table 5.

TABLE 5

Decomposition Rate of 5-fluoro-2'-deoxyuridine in Homogenates of Rat Organs and Plasma

| Homogenate and plasma conc. | Case number | Decomposition rate constant $hr^{-1}$ |
|---|---|---|
| 0.1% small intestine | 5 | 2.6568 ± 0.2011 |
| 0.4% liver | 5 | 0.6014 ± 0.0841 |
| 0.4% kidney | 4 | 0.4200 ± 0.0288 |
| 20% plasma | 4 | <0.001 |

As can be seen from Table 5, pyrimidine nucleoside phosphorylase activity is markedly higher in the small intestine as compared with that in other organs, and this fact markedly restricts the effectiveness of a pyrimidine type nucleic acid derivative in oral administration.

Test Example 6

Effect of Enzyme Activity Inhibitor on Pyrimidine Nucleoside Phosphorylase Activity in Rat Small Intestine and Beagle Small Intestine Inhibitory effects of 1-[(2-hydroxyethoxy)methyl]-5-methyluracil, 1-[(2-hydroxyethoxy)methyl]-5-fluorouracil, 1-[(2-hydroxyethoxy)methyl]-5-bromouracil on pyrimidine nucleoside phosphorylase activity in the small intestine homogenates of an SD-strain male rat and a male beagle were assayed with a lowering in decomposition rate of 5-fluoro-2'-deoxyuridine (concentration: 0.025 mM) and compared with the same effects of thymidine and deoxyuridine.

The results are shown in Table 6.

TABLE 6

Effect of Enzyme Inhibitor on Decomposition Rate of 5-fluoro-2'-deoxyuridine in Rat Small Intestine and Beagle Small Intestine

| Effect on 0.09% w/v Rat Small Intestine Homogenate (pH 7.0, 37° C.) | | | |
|---|---|---|---|
| Inhibitor conc. | Half-life of 5-fluoro-2'-deoxy-uridine | Inhibitory percentage | Half-life of inhibitor |
| No addition (5-fluoro-2'-deoxyuridine 0.025 mM) | 17.0 min. | 0% | — |
| Thymidine (control composition) 0.025 mM | 30.6 min. | 44.4% | 88.5 min. |
| Deoxyuridine (control composition) 0.025 mM | 22.2 min. | 23.4% | 65.9 min. |
| 1-[(2-Hydroxyethoxy)-methyl]-5-methyluracil (composition of the invention) 0.025 mM | 100.6 min. | 83.1% | >1000 min. |
| 1-[(2-Hydroxyethoxy)-methyl]-5-fluorouracil (composition of the invention) 0.025 mM | 49.4 min. | 65.6% | >1000 min. |
| 1-[(2-Hydroxyethoxy)-methyl]-5-bromouracil (composition of the invention) 0.01 mM | 32.5 min. | 47.7% | >1000 min. |

| Effect of 0.4% w/v Beagle Small Intestine Homogenate (pH 7.0, 37° C.) | | | |
|---|---|---|---|
| Inhibitor conc. | Half-life of 5-fluoro-2'-deoxy-uridine | Inhibitory percentage | Half-life of inhibitor |
| No addition (5-fluoro-2'-deoxyuridine 0.025 mM) | 27.8 min. | 0% | — |
| Thymidine (control composition) 0.025 mM | 58.1 min. | 52.2% | 27.0 min. |
| Deoxyuridine (control composition) 0.025 mM | 30.5 min. | 8.8% | 32.3 min. |
| 1-[(2-Hydroxyethoxy)-methyl]-5-methyluracil (composition of the inventon) 0.025 mM | 85.1 min. | 67.3% | >1000 min. |
| 1- [(2-Hydroxyethoxy)-methyl]-5-fluorouracil (composition of the invention) 0.025 mM | 46.8 min. | 40.6% | >1000 min. |
| 1-[(2-Hydroxyethoxy)-methyl]-5-bromouracil (composition of the | 62.5 min. | 55.5% | >1000 min. |

TABLE 6-continued

Effect of Enzyme Inhibitor on Decomposition Rate of 5-fluoro-2'-deoxyuridine in Rat Small Intestine and Beagle Small Intestine invention) 0.01 mM As shown in Table 6, it can be understood that the decomposition of 5-fluoro-2'-deoxyuridine in the intestine of a rat and a beagle is inhibited by thymidine phosphorylase, because it is more potency inhibited by thymidine than by deoxyuridine.

Also, it can be seen that the 1-[(2-hydroxyethoxy)methyl]uracils represented by the formula (II) in item 1 of the scope of claim for patent inhibit potent inhibitory activity against the thymidine phosphorylase activity and that they are themselves enzymatically stable.

Reference Example 1

Synthesis of 1-[[2-(Hexadecanoyloxy)-ethoxy]-methyl]-5-methyluracil

To a solution of 200 mg (1.0 mmol) of 1-[(2-hydroxyethoxy)-methyl]-5-methyluracil in 10 ml of anhydrous pyridine was added 545 mg (1.1 mmol) of palmitic anhydride for about one hours, and the mixture was stirred overnight at room temperature. The reaction mixture was added 2N HCl to adjust pH 4.00, and the reaction product was extracted three times with 20 ml of chloroform. Chroroform was distilled away at room temperature under reduced pressure and the obtained crude product was purified by column chromatography on silica gel. The chloroform-ethanol (97:3 to 96:4) eluants were collected and concentrated to yield 1-[[2-(hexadecanoyloxy)-ethoxy]-methyl]-5-methyluracil. The yield was 80%. The analytical data are as follows.

UV (λmax in ethanol): 207 nm, 263 nm,

NMR ($\delta_{CDCl_3}^{TMS}$): 0.8–0.9 (t. 3H), 1.2–1.4 (m. 26H), 1.9 (d. 3H), 2.3–2.4 (t. 2H), 3.6–3.8 (m. 2H), 4.1–4.3 (m. 2H), 5.1 (s. 2H), 7.1 (m. 1H), 10.0 (s. 1H), m.p.: 78°–79° C.

Reference Example 2

Synthesis of 1-[[2-(Octadecanoyloxy)-ethoxy]-methyl]-5-methyluracil

To a solution of 200 mg (1.0 mmol) of 1-[(2-hydroxyethoxy)-methyl]-5-methyluracil in 10 ml of anhydrous pyridine was added 606 mg (1.1 mmol) of stearic anhydride for about one hours, and the mixture was stirred overnight at room temperature. The reaction mixture was added 2N HCl to adjust pH 4.00, and the reaction product was extracted three times with 20 ml of chloroform. Chroroform was distilled away at room temperature under reduced pressure and the obtained crude product was purified by column chromatography on silica gel. The chloroform-ethanol (98:2 to 97:3) eluants were collected and concentrated to yield 1-[[2-(octadecanoyloxy)-ethoxy]-methyl]-5-methyluracil. The yield was 80%. The analytical data are as follows.

UV (λmax in ethanol): 207 nm, 263 nm,

NMR ($\delta_{CDCl_3}^{TMS}$): 0.8–0.9 (t. 3H), 1.2–1.4 (m. 30H), 1.9 (d. 3H), 2.3–2.4 (t. 2H), 3.6–3.8 (m. 2H), 4.1–4.3 (m. 2H), 5.1 (s. 2H), 7.1 (m. 1H), 10.0 (s. 1H), m.p.: 85°–86° C.,

Reference Example 3

Synthesis of 1-[[2-(Eicosanoyloxy)-ethoxyl]-methyl]-5-methyluracil

To a solution of 200 mg (1.0 mmol) of 1-[(2-hydroxyethoxy)-methyl]-5-methyluracil in 10 ml of anhydrous pyridine was added 668 mg (1.1 mmol) of arachidic anhydride for about one hours, and the mixture was stirred overnight at room temperature. The reaction mixture was added 2N HCl to adjust pH 4.00, and the reaction product was extracted three times with 20 ml of chloroform. Chroroform was distilled away at room temperature under reduced pressure and the obtained crude product was purified by column chromatography on silica gel. The chloroform-ethanol (99:1 to 98:2) eluants were collected and concentrated to yield 1-[[2-(eicosanoyloxy)-ethoxy]-methyl]-5-methyluracil. The yield was 80%. The analytical data are as follows.

UV (λmax in ethanol): 207 nm, 263 nm,

NMR ($\delta_{CDCl_3}^{TMS}$): 0.8–0.9 (t. 3H), 1.2–1.4 (m. 34H), 1.9 (d. 3H), 2.3–2.4 (t. 2H), 3.6–3.8 (m. 2H), 4.1–4.3 (m. 2H), 5.1 (s. 2H), 7.1 (m. 1H), 10.0 (s. 1H), m.p.: 93°–94° C.,

Example 1

| Preparation of Tablets of the Present Invention | |
|---|---|
| Active ingredients (3',5'-didodecanoyl-5-fluoro-2'-deoxyuridine 25 mg 1-[[2-(octadecanoyloxy)ethoxy] methyl[-5-methyluracil 25 mg) | 50 mg |
| Lactose | 50 mg |
| Corn starch | 40 mg |
| Carboxymethyl cellulose calcium | 57 mg |
| Magnesium stearate | 3 mg |
| Total | 200 mg |

Tablets were prepared in a conventional manner by use of the above components.

Example 2

Preparation of Injectable Preparation of the Invention

The components of the present invention, 3',5'-diacetyl-5-fluoro-2'-deoxyuridine and 1-[[2-(hexanoyloxy)ethoxy]methyl]-5-methyluracil were dissolved in an aqueous solution (pH 6.00–7.50) to obtain injectable preparations containing 0.3 to 1.0 mg of each compound per 1 ml.

Example 3

| Preparation of Capsules of the Invention | |
|---|---|
| Active ingredients (3',5'-ditetradecanoyl-5-fluoro-2'-deoxyuridine 25 mg, 1-[[2-(eicosanoyloxy) ethoxy]methyl]-5-methyluracil 25 mg) | 50 mg |
| Lactose | 97 mg |
| Crystalline cellulose | 50 mg |
| Magnesium stearate | 3 mg |
| Total | 200 mg |

By use of the above components, capsules were prepared in a conventional manner.

Example 4

| Prepartion of Suppositories of the Invention | |
|---|---|
| Active ingredients | 50 mg |
| (3',5'-dihexadecanoyl-5-fluoro-2'-deoxyuridine 25 mg, 1-[[2-docosanoyloxy)ethoxy]methyl]-5-bromouracil 25 mg) | |
| Witepp sol | 950 mg |
| Total | 1000 mg |

By use of the above components, suppositories were prepared in a conventional manner.

Example 5

| Preparation of Granules of the Invention | |
|---|---|
| Active ingredients | 50 mg |
| (3',5'-ditoluoyl-5-fluoro-2'-deoxyuridine 25 mg, 1-[[2-(benzoyloxy)ethoxy]methyl]-5-methyluracil 25 mg) | |
| Lactose | 587 mg |
| Ethyl cellulose | 10 mg |
| Corn starch | 250 mg |
| Carboxymethyl cellulose calcium | 100 mg |
| Magnesium stearate | 3 mg |
| Total | 1000 mg |

By use of the above components, granules were prepared in a conventional manner.

Example 6

| Preparation of Tablets of the Present Invention | |
|---|---|
| Active ingredients | 50 mg |
| (5-fluoro-2'-deoxyuridine 25 mg; 1-[(2-hydroxyethoxy)methyl]-5-methyluracil 25 mg) | |
| Lactose | 50 mg |
| Corn starch | 40 mg |
| Carboxymethyl cellulose calcium | 57 mg |
| Magnesium stearate | 3 mg |
| Total | 200 mg |

Example 7

| Preparation of Capsules of the Present Invention | |
|---|---|
| Active ingredients | 100 mg |
| (5-fluoro-2'-deoxyuridine 25 mg; 1-[(2-hydroxyethoxy)methyl]-5-methyluracil 25 mg) | |
| Lactose | 97 mg |
| Crystalline cellulose | 50 mg |
| Magnesium stearate | 3 mg |
| Total | 250 mg |

Example 8

Preparation of Enteric Soluble Tablets of the Present Invention

The tablets prepared in Example 1 were coated with 35 mg of hydroxypropylmethyl cellulose phthalate.

Example 9

| Preparation of Granules of the Present Invention | |
|---|---|
| Active ingredients | 50 mg |

-continued

| Preparation of Granules of the Present Invention | |
|---|---|
| (5-fluoro-2'-deoxyuridine 25 mg and 1-[(2-hydroxyethoxy)methyl]-5-methyluracil 25 mg) | |
| Lactose | 587 mg |
| Ethyl cellulose | 10 mg |
| Corn starch | 250 mg |
| Carboxymethyl cellulose calcium | 100 mg |
| Magnesium stearate | 3 mg |
| Total | 1000 mg |

Example 10

Preparation of Enteric Soluble Capsules of the Present Invention

The granules prepared in Example 5 were coated with 250 mg of cellulose acetate phthalate and filled in five gelatin hard capsules each in an amount of 250 mg.

What is claimed is:

1. An antitumor composition containing, as effective ingredients in pharmaceutically effective amounts, (i) at least one pyrimidine type nucleic acid derivative having the formula (I):

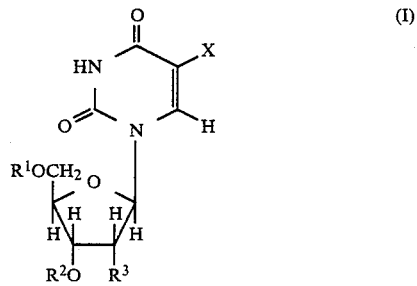

wherein X represents a fluorine atom or a trifluoromethyl group, $R^1$ and $R^2$ may be the same or different and represent a hydrogen atom, an aliphatic acyl group having 4 to 24 carbon atoms or an aromatic acyl group having 7 to 12 carbon atoms, $R^3$ represents a hydrogen atom or a hydroxyl group, and (ii) at least one 1-[(2-hydroxyethoxy)methyl]uracil derivative having the formula (II):

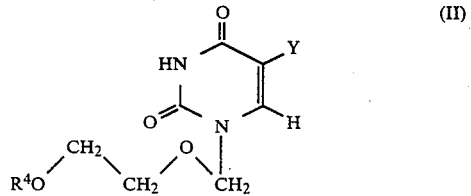

wherein Y represents a hydrogen atom, a halogen atom, a methyl group, a benzyl group, a benzyloxybenzyl group, a vinyl group, a nitro group, or an amino group and $R^4$ represents a hydrogen atom, an aliphatic acyl group having 2 to 24 carbon atoms or an aromatic acyl group having 7 to 12 carbon atoms.

2. An antitumor composition as claimed in claim 1, wherein $R^1$ and $R^2$ are acyl groups and $R^3$ is a hydrogen atom in the formula (I) and $R^4$ is an acyl group in the formula (II).

3. An antitumor composition as claimed in claim 1, wherein $R^4$ in the formula (II) is an aliphatic acyl group having 2 to 24 carbon atoms or an aromatic acyl group having 7 to 12 carbon atoms.

4. An antitumor composition as claimed in claim 1, wherein $R^1$ and $R^2$ in the formula (I) are aliphatic acyl groups having 4 to 24 carbon atoms or aromatic acyl groups having 7 to 12 carbon atoms.

5. An antitumor composition as claimed in claim 1, wherein $R^1$, $R^2$, and $R^3$ are hydrogen atoms in the formula (I) and $R^4$ is a hydrogen atom in the formula (II).

6. An antitumor composition as claimed in claim 1, wherein the component (i) and the component (ii) are formulated at a molar ratio of 1: 0.1 to 1: 20.

7. An antitumor composition as claimed in claim 1, wherein the component (i) and the component (ii) are formulated at a molar ratio of 1: 0.5 to 1: 5.

8. An antitumor composition as claimed in claim 1, which is in the form of an orally administratable preparation.

9. An antitumor composition as claimed in claim 8, wherein the orally administratable preparation is in the form of powders, capsules, tablets, liquid, granules or pills.

10. An antitumor composition as claimed in claim 1, which is in the form of a suppository preparation.

11. An antitumor composition as claimed in claim 9, which is coated with a coating of an enteric soluble substance.

12. A kit for use in the treatment of tumors comprising the component (i) of claim 1 and, physically separate therefrom, the component (ii) of claim 1.

13. A method for treating tumors, which comprises administering pharamaceutically effective amounts of the component (i) of claim 1 and the component (ii) of claim 1 to a warm-blooded animal.

* * * * *